United States Patent [19]

Szoka

[11] Patent Number: 4,483,929
[45] Date of Patent: Nov. 20, 1984

[54] LIPOSOMES WITH GLYCOLIPID-LINKED ANTIBODIES

[75] Inventor: Frank C. Szoka, San Francisco, Calif.

[73] Assignee: Liposome Technology Incorporated, Menlo Park, Calif.

[21] Appl. No.: 374,031

[22] Filed: May 3, 1982

[51] Int. Cl.³ .................... G01N 33/54; G01N 33/58
[52] U.S. Cl. ........................ 436/533; 435/7; 435/8; 436/512; 436/532; 436/534; 436/548; 436/800; 436/803; 436/819; 436/828; 436/829
[58] Field of Search ............... 436/512, 532, 533, 534, 436/808, 828, 829; 422/61; 435/7

[56] References Cited

U.S. PATENT DOCUMENTS

| | | | |
|---|---|---|---|
| 3,995,018 | 11/1976 | Sjoquist | 436/828 X |
| 4,193,983 | 3/1980 | Ullman | 436/819 X |
| 4,200,436 | 4/1980 | Mochida | 436/512 |
| 4,235,792 | 11/1980 | Hsia | 436/817 X |
| 4,255,411 | 3/1981 | Lim | 436/815 X |
| 4,342,739 | 8/1982 | Kakimi | 436/823 X |
| 4,372,745 | 2/1983 | Mandle | 422/61 X |
| 4,376,110 | 3/1983 | David | 436/529 X |

OTHER PUBLICATIONS

T. J. Williams et al., Archives of Biochemistry and Biophysics, 195(1), 145–151 (1979).
D. Sinha et al., Biochemical and Biophysical Research Communications, 90(2), 554–560 (1979).
A. Huang et al., The Journal of Biological Chemistry, 255(17), 8015–8018 (1980).
G. S. Bethel et al., The Journal of Biological Chemistry, 254(8), 2572–2574 (1979).
T. D. Heath et al., Biochimica et Biophysica Acta, 640, 66–81 (1981).

*Primary Examiner*—Sidney Marantz
*Attorney, Agent, or Firm*—Ciotti & Murashige

[57] ABSTRACT

Lipid vesicles, labelled with encapsulated reporter compositions and bound to antibodies comprise a new class of immunoreagent, useful in immunoassays for ligands.

9 Claims, No Drawings

LIPOSOMES WITH GLYCOLIPID-LINKED ANTIBODIES

BACKGROUND OF THE INVENTION

1. Field of the Invention

The invention relates to immunoassaying of organic compounds and more particularly relates to a novel class of reagents useful for such immunoassaying.

2. Brief Description of the Prior Art

Immunochemical reactions have served as a basis for the assay of a wide variety of organic compounds (particularly biologically active compounds) for many years.

The term "immunochemical reaction" is used herein to refer to that class of chemistry known as "immunochemistry". Immunochemistry is chemistry classically concerned with the physical interaction between "antigens" and "antibodies".

"Antigens" are high molecular weight compounds, usually protein or protein-polysaccharide complexes, which upon entry in the blood stream of a vertebrate stimulate the transformation of the small lymphocytes of the B-type into lymphoblasts. The lymphoblasts synthesize and secrete "antibodies" specific to the antigen stimulator. The antibodies are proteins possessing reactive sites specifically complimentary to a reactive feature or site on the stimulating antigen. Antibodies generally have the property of rendering the antigen harmless to the host organism, by occupying the immunologically active sites on the antigen molecules, and sometimes also by forcing precipitation or agglutination of the antigen, or by other protective mechanisms.

In some but not all applications it becomes difficult or meaningless to maintain the classical distinction between antigen and antibody, because in many regards the relation between antigen and antibody is reciprocal and each precipitates or agglutinates the other. The basis for the distinction resides in the history of the particular substance, and this can become irrelevant outside the original antibody-generating organism, for example in reagent applications. More specifically, and as an illustration, immunoglobulins such as IgA, IgG, IgM, IgD and IgE are by the above definitions antibodies (actually a class of antibodies) since they are produced by plasma cells of the lymphoid system in response to the presence of an antigen (usually a multiplicity of antigens). However, the immunoglobulins can also be antigenic in behavior and responsible for the production of the specific antibodies known as anti-IgA, anti-IgG, anti-IgM, anti-IgD and anti-IgE, respectively. For this reason the antigen-antibody relationship may be advantageously described in this reciprocal way: an antibody is the "immunological-homologue" of the antigen which produced it, and vice versa. An antibody and its corresponding antigen are thus homologues of each other. They may also be said to be homologous to each other.

In any event, the immunochemical antigen-antibody relationship forms the basis for immunoassay of either "homologue". Procedurally, the various known techniques of immunoassay for the immunoreactant homologues (antigen, antibody), i.e.; radioimmunoassay, fluorescent immunoassay and enzyme immunoassay are substantially identical. Each technique comprises, in general, the separation of bound and labeled immunoreactant from unbound, labeled immunoreactant. This may be done, for example by immobilizing one of the immunoreactants, labeling one of the immunoreactants with a marker or tag to monitor its presence and reacting the immobilized immunoreactant with the free immunoreactant and measuring the degree of reaction through monitoring of the labeled immunoreactant. The main difference between the various techniques resides in utilization of different reagents as markers or tags for visualization and measurement of the immunoreaction.

Radioimmunoassay is a popular and highly sensitive technique, particularly when the material being assayed for is in relatively small concentrations. It has found commercial acceptance. However, radioimmunoassay procedures are not entirely satisfactory for all purposes. The reagents employed are of limited stability and shelf-life. Their use is often subject to special handling and license. Personnel carrying out the procedure require special protection, special facilities and extraordinary training. The art has been searching for equally sensitive immunoassay procedures, employing non-radioactive reagents.

Among immunoassay procedures which obviate the need for radioactive reagents is the so-called spin membrane immunoassay technique (see for example U.S. Pat. No. 3,850,578). The technique is based on the fact that a lipid-linked antigen may be solubilized in a lipid bilayer membrane matrix to form antigen sensitized (bound) lipid vesicles. The sensitized vesicles, encapsulating spin resonance labels, will bind antibodies through the active, bound antigen. The antigen-antibody bound vesicles are disposed to lysis under certain conditions wherein those lipid vesicles not attached to antibody will not lyse. Release of the encapsulated spin labels is measurable to determine therefore the quantity of bound antibody. The method does not measure, at least directly, the presence of antigen, but only antibody.

The immunoassay of the present invention combines the sensitivity of a radioimmunoassay with the advantages of the spin membrane immunoassay, without the need for radioactive reagents. This sensitivity is greater than obtained in the spin membrane immunoassay. More specifically, in the immunoassay of the present invention, as the quantity of compound assayed for increases, the signal generated by the assay technique increases proportionately. In contradistinction, the signal generated by the spin membrane immunoassay technique decreases as the quantity of compound assayed for increases. Thus, sensitivity of the method of the invention is greater [this is due to the fact that the signal from totally lysed vesicle (no antibody present) and the lysis that occurs when a small quantity of antibody is present is the difference between two large numbers and thus the signal to noise ratio is low]. In the method of the invention, when no antigen is present, very little signal is given off. The assay is therefore simpler to interpret.

Another advantage of the immunoassay of the invention resides in the reagent, prepared by coupling antibody to a lipid vesicle surface. The same method of coupling may be used regardless of the antibody or vesicle composition used. In contradistinction, the prior art spin lable immunoassay requires different amphipathetic vesicle molecules for attaching different antigens.

Still another advantage of the immunoassay of the invention resides in the ability to use a wide variety of different reporter compositions. In the spin membrane immunoassay one is restricted to the use of spin lable compositions and in a radioimmunoassay one is restricted to using radioactive reporter compositions. This is an important advantage since one can prepare reagent lipid vesicles with different reporter compositions encapsulated in different vesicles, to which different antibodies are attached. Specific antibodies, for example one to insulin and one for glucagon, may be attached to the two different sensitized vesicle preparations and the two compounds may be assayed for simultaneously in a single procedure.

The preferred reagents of the invention are prepared from very pure forms of antibodies, which account for their high degree of sensitivity to specific antigens. This high degree of specificity is a distinct advantage in use of the reagents for clinical (medical) diagnostic purposes.

Other advantages associated with the reagents and immunoassay of the invention will be described more fully hereinafter.

SUMMARY OF THE INVENTION

The invention comprises a reagent which is useful for the immunoassay of a chemical compound capable of entering into an immunochemical reaction with a known antibody, which comprises;

a fluid dispersion of a plurality of homogeneous immunoreactant particles, said particles comprising a water-soluble, non-radioactive reporter composition encapsulated within a lipid vesicle;

each of said vesicles having bound to its outer surface a specific highly purified polyclonal antibody or a monoclonal antibody possessive of an active epitopic site which is capable of immunochemical reaction with said compound and which will be lysed in the presence of a lysing agent when the epitopic site is occupied by an immunochemical reaction.

The reagents of the invention are useful to assay for chemical compounds capable of entering into an immunochemical reaction with a corresponding antibody, i.e.; a ligand, provided the ligand is not capable by itself of lysing the lipid vesicle portion of the reagent of the invention. The ligands assayed for by the method of the invention may be monoepitopic or polyepitopic and include for example polypeptides, proteins, polysaccharides, nucleic acids, combinations thereof and the like. Representative proteins assayable by the method of the invention are a wide variety of:

protamines,
histones,
albumins,
globulins,
scleroproteins,
phosphoproteins,
mucoproteins,
chromoproteins,
lipoproteins,
nucleoproteins,
glycoproteins and the like;

Representative of specific polypeptide and protein hormone ligands advantageously assayable for by the method of the invention are:

parathyroid hormone (parathromone),
thyrocalcitonin,
insulin,
glucagen,
relaxin,
erythroporetin,
melanotropin (melanocyte-stimulating),
somatotropin,
corticotropin (adrenocorticotropic hormone),
thyrotropin,
follicle-stimulating hormone,
luteinizing hormone (interstitial cell-stimulating hormone),
gonadotropin, prolactin, pepsin
and the like.

Other ligands include a wide variety of drugs, metabolites, virus derived antigens (such as hepatitus B surface antigen), bacterial antigens and derived antibodies (such as syphillis antibodies), parasite derived antigens, allergens and the like. Included among drugs of interest are alkaloids and their metabolites; barbiturates and their metabolites; aminoalkylbenzenes such as the amphetamines, catecholamines, their metabolites and derivatives; prostaglandins, which differ by degree and sites of hydroxylation and unsaturation; antibiotics, their metabolites and derivatives; nucleosides and nucleotides, and the like.

The invention also comprises the use of the reagents of the invention for the immunoassay of chemical compounds capable of immunochemical reaction with the antibody bound to the lipid vesicle.

The term "reporter composition" as used herein means a water-soluble, non-radioactive compound or composition containing a non-radioactive compound which is either directly or indirectly involved with the production of a detectable and measurable signal upon release from encapsulation. Representative of reporter compositions are water-soluble chromogens, e.g. fluorescers and chemiluminescers, catalysts, both enzymatic and non-enzymatic, molecules having an enzymatically labile bond which upon enzymatic cleavage provides a compound which can be detected, either directly or indirectly, and the like. More specific examples of reporter compositions will be provided hereinafter.

The term "non-radioactive" as used throughout the specification and claims means a chemical compound, isotope or composition (usually having an atomic weight over 207) which does not exhibit radioactivity, i.e.; spontaneous nuclear disintegration (unaffected by chemical or physical influences) of the compound, isotope or composition with emission of nucleons or of electromagnetic radiation.

The term "lipid vesicle" as used throughout the specification and claims means a man-made (synthetic) liposome.

DETAILED DESCRIPTION OF THE PREFERRED EMBODIMENTS OF THE INVENTION

Lipid vesicles (synthetic liposomes) have been known for a number of years as convenient carriers of encapsulated water soluble materials. Several methods are available to make lipid vesicles, encapsulating water-soluble materials; see for example Bangham et al. in J. Mol. Biol., 13:238–252 (1965); D. Papahadjopoulos and N. Miller (Biochim. Biophys. Acta, 135:624–638[1967]); Batzri and Korn (Biochim. Biophys. Acta, 2981015 [1973]); Deamer and Bangham in Biochim. Biophys. Acta, 443:629–634 (1976); Papahadjopoulos et al. in Biochim. Biophys. Acta, 394:483491 (1975); German Pat. No. 2,532,317; and U.S. Pat. Nos. 3,804,776; 4,016,100 and 4,235,871.

Lipid vesicle wall forming compounds are generally well known as are the methods of their preparation. For example, any number of phospholipids or lipid compounds may be used to form the vesicle walls. Representative of such wall forming compounds are those described in the U.S. Pat. No. 4,235,871, the disclosure of which is hereby incorporated herein by reference thereto.

The lipid vesicles employed in the present invention are prepared, encapsulating reporter compositions as defined above. The lipid vesicles so prepared contain within their aqueous space part of an amplification system that will provide an observable signal when a hole is made in the vesicle bilayer, releasing the reporter composition. The amplification system can generate a signal which can be detected by a variety of methods appropriate to the nature of the amplification system, e.g.; fluorescence, spectrophotometric, or other electromagnetic signals such as that arising from luminescence or even electropotential. The signal is generated when the reporter composition inside the vesicle escapes to the outside when a hole is made in the vesicle membrane bilayer or when material outside the vesicle enters to mix with the reporter composition such as when a substrate outside the vesicle enters and can interact with an enzyme type of reporter composition inside the lipid vesicle.

Water-soluble, non-radioactive reporter compositions are widely known as is the method of their preparation. Representative of reporter compositions are chromogens which both absorb and emit light, i.e.; fluorescers. Representative of fluorescers are:
3,6-dihydroxy-9-phenylxanthydrol,
2-amino-6-sulfonatonaphthalene, bis(3'-aminopyridinium) and the like.

The fluorescing chromogen will preferably absorb light at wavelengths longer than 350 nm, more preferably longer than 400 nm, and particularly preferred longer than 450 nm. The extinction coefficient is preferably greater than $10^4$ above 400 nm, preferably greater than $10^4$ above 450 nm and more preferably greater than $10^5$ above 400 nm. Preferably, the fluorescer emits light above 400 nm, more preferably above 450 nm.

Preferred fluorescers encapsulated as reporter compositions and used in preparing the reagents and in the method of the invention are those which are self-quenching, i.e.; those which exhibit a decrease in fluorescence emission as its concentration increases above a certain, given value. Representative of such self-quenching fluorescers are carboxyfluorescein (Szoka et al. BBA 551, 295–303, 1979) or Calcein (Allen and Clel- and BBA 597,418–426 1980). A wide variety of other fluorescent molecules may be used, quenched by the Stern-Volmer effect. For example 8-amino-1,3,6-naphthalenetrisulfonate (ANTS) will quench in the presence of high concentrations of thallium chloride. In all amplification systems of this type lysis of the lipid vesicle in the presence of bound ligand results in the contents of the vesicle being dispersed in the far greater volume of the dispersing solution outside of the vesicle, with a reversal of the quenched condition. Under these conditions of reversal, the fluorescence signal increases in direct proportion to the release by vesicle lysis.

Another class of fluorescers involves those which upon forming a complex with a non-fluorescing molecule become highly fluorescent. An example of such a complex is that formed between Terbium and dipicolinic acid as described by Wilchut and Papahadjopoulos, Nature 281, 690–692 (1979).

Alternative reporter compositions are represented by compounds which are chemiluminescent. A chemiluminescent compound is one which becomes eletronically excited by a chemical reaction and may then emit light which serves as the detectable signal or donates energy to a fluorescent acceptor. Chemiluminescent compounds may be divided into two classes. The two classes are (1.) those which do not involve intermediacy of enzyme catalysis and (2.) those which do involve enzyme catalysis.

A diverse number of families of compounds of the first class have been found to provide chemiluminescence under a variety of conditions. One family of compounds is 2,3-dihydro-1,4-phthalazinediones such as luminol, which is the 5-amino analog. Other members of the family include the 5-amino-6,7,8-trimethoxy and the dimethylamino[ca]benz analogs. These compounds can be made to luminesce with alkaline hydrogen peroxide or calcium hypochlorite and a base. Another family of compounds is the 2,4,5-triphenylimidazones. Chemiluminescent analogs include para-dimethylamino and -methoxy substituted compounds.

Another group of chemiluminescent compounds are the indolen-3-yl hydroperoxides, precursors thereto and derivatives thereof. Still another group of such compounds are the bis-9-9'-biacridinium salts of which lucigenin, N,N'-dimethyl-9-9'-biacridinium dinitrate is illustrative. These compounds chemiluminesce upon combination with alkaline hydrogen peroxide. Still another group of such compounds are the acridinium salts which are substituted in the 9 position. Particular substituents are carboxylic esters particularly the aryl esters, acyl substituents, particularly benzoyl, and cyano. Alkaline hydrogen peroxide is employed to induce chemiluminescence in this last group.

Another source of chemiluminescence are the hydroperoxides, e.g.; tetralin hydroperoxide, in combination with metal complexes, particularly porphyrins and phthalocyanines, where the metals are iron and zinc.

Preferred amplification systems are those which provide a satisfactory quantum efficiency of emission from the chemiluminescer at a pH at or below 11, preferably at or below 10.

Chemiluminescent compounds of the second class, i.e.; those which chemiluminesce under enzymatic catalysis may be further classed into, primarily two groups. The first group are those compounds which chemiluminesce in combination with alkaline hydrogen peroxide. By employing a peroxidase e.g. horse radish peroxidase, in combination with hydrogen peroxide and the chemiluminescer, chemiluminescence can be achieved. Illustrative of the group are 2,3-dihydro-1,4-phthalazinediones.

The second group of enzymatic sources of chemiluminescence is based on luciferins and their analogs and luciferases. Of particular importance are bacterial luciferases.

In a preferred embodiment of the invention, the reagent lipid vesicle encapsulates an enzyme substrate that can be cleaved when released from containment in the lipid vesicle, into a colorimetric or fluorescent product by an enzyme outside the lipid vesicle. Such enzyme substrates are well known to those skilled in the art (see for example H. Bergmeyer Ed. Verblagchemie, N.Y. 1978). Alternatively the enzyme can be encapsulated inside the lipid vesicle and the substrate can be on the outside. Lysis of the lipid vesicle following the combining of the sensitized lipid vesicle reagent with antigen allows the substrate to enter the lipid vesicles, mix with the enzyme and be cleaved to a colored or fluorescent signaling product. As an example, the lipid vesicle reagent employed may be one which encapsulates an enzyme, such as a peroxidase. The analyte will have added to it a chromogenic system or enzyme substrate which will react with the enzyme to develop color or fluorescence. A chromogenic system or substrate may be one containing hydrogen peroxide and a reduced (colorless) chromogen such as the redox type of indicator dye capable of color development upon exposure to an oxidizing agent such as hydrogen peroxide. Representative of such are 3,3'-diaminobenzidine, p-diphenylamine sulfonic acid, o-tolidine dihydrochloride, m-toluidine, benzidine, quaiacol, 2,7-diaminofluorene, o-dianisidine, and the like and mixtures thereof. Preferred as a chromogen is 2,2-azino-di-(3-ethylbenzothiazoline-6-sulphonic acid).

When the chromogen is mixed with hydrogen peroxide, a chromogenic reagent or system is obtained which will turn color in the presence of the enzyme released upon lysis of the lipid vesicle, to a degree determined by the quantity of enzyme present (and hence the quantity of bound antigen analyte). The reaction which occurs may be represented schematically by the equation:

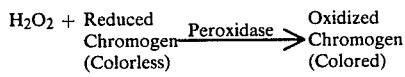

Full color development is generally obtained within about 1 hour. The color developed can be observed visually or with the aid of a spectrophotometer or a like means of measuring color. By comparison with known standards, the quantity of analyte can be readily determined.

Another type of reporter composition is the electron spin resonance labeled molecules such as those described in the U.S. Pat. No. 3,850,578. The preferred labels are nitroxides, detectable upon release from a lysed lipid vesicle by an electron paramagnetic resonance spectrometer. The technique of signal measurement is described in the U.S. Pat. No. 3,850,578.

It should be emphasized that the lipid vesicle can contain a variable number of reporter molecules and this number can be varied from a few to 10,000,000 per vesicle depending on the size of the vesicle and the concentration of the substance in the vesicle aqueous space. When the vesicle is lysed by the lytic agent these encapsulated molecules are all able to interact with molecules in the external solution. If the entrapped reporter substance is an enzyme, then an additional amplification step can be achieved since enzyme can convert a large number of substrate molecules to signal giving products.

To prepare the immunochemical reagents of the invention, antibodies are bound to the membrane surface of the lipid vesicle, encapsulating the reporter composition. Binding may be chemical to produce a "sensitized" lipid vesicle or reagent vesicle. The term "chemically bound" as used herein means a binding caused by the interaction of individual atoms. Chemical bonding comprises, for example, covalent bonding, hydrogen bonding, hydrophobic bonding, intercalation and the like. Prior to the present invention, techniques for bonding antibodies to the surface of lipid vesicles were crude and only minimal densities of attachment were achieved. With newly developed techniques the antibody may be directly bound to the lipid membrane surface of the lipid vesicle or, depending on the composition of the lipid membrane, may be linked through a modified membrane surface. For example, a convenient means of binding is by first oxidizing the carbohydrate portion of the lipid vesicle membrane to convert alcohol groups to aldehyde groups, such as by exposure to sodium metaperiodate. The resulting aldehyde groups will couple antibody to the membrane surface, following the method of Fiddler and Gray, Analyt. Biochem., 86, 716–724, (1978).

Modification of the membrane surfaces will, of course, depend upon the lipid composition of the membranes. When, for example, a galactose lipid is present, oxidation of the group at the C-6 position will provide a reactive group which will covalently bond an antibody.

Those skilled in the art will readily appreciate that to increase the flexibility of the immunoassay it would be advantageous to prepare a lipid vesicle reagent that could be used as a reagent in many different assays, i.e.; a "universal reagent". By changing the antibody that one uses you would have an assay for the antigen that the antibody recognizes. To accomplish this a fragment of an antibody that recognizes other antibodies may be attached to the lipid vesicle surface. The portion of the antibody that is recognized by complement is first removed by treatment with an enzyme (pepsin) as described by Nisonoff and Rivers, Arch. Biochem. Biophys. 93, 460–470, 1961.

Antibody can also be bound to the vesicle surface through a binding molecule, such as an intermediary protein which will recognize and bind to the Fc region on the antibody. Representative of such a protein is the bacterial Protein A. Protein A has amino acid side chains which will attach to the lipid vesicle membrane following the general procedure of Fiddler and Gray, supra. Other intermediary proteins include fragments of antibodies such as the Fab fragment of an anti-IgG antibody. The Fab does not activate complement, hence one can prepare a single batch of vesicles, attach the Fab fragment and use this as the starting material for different assays. In this case the specific antibody would be attached to the vesicle through the Fab fragment giving one a versatile, stable assay reagent. Fab fragments such as the F(ab') and F(ab')2 fragments are advantageously used.

However, bridges, crosslinks and modifications to the vesicle are not essential to the preparation of the reagents of the invention. Satisfactory reagents may be prepared by simple adsorption or intercalation of antibodies modified by the attachment of a hydrophobic anchor (Sinha & Karush, Biochem. Biophys. Res. Commun. 90, 554–560 1979) to the lipid vesicle membrane. This can be accomplished by incubating the lipid vesicles with the modified antibody, to promote sensitized lipid vesicles, i.e.; lipid vesicle reagents which will bind with corresponding antigen.

The density or proportion of antibody attached to the lipid vesicles is important, in regard to the reactivity or sensitivity of the reagents of the invention and to the sensitivity of any immunoassay which employs the reagents of the invention. Unless a minimum density of attachment is achieved, the reagents will lack the desired avidity and sensitivity.

Preferably, to obtain highly sensitive sensitized vesicle reagent, antibody is attached to the vesicles in a minimum density. For vesicles having mean number average diameters of about 2000 A°, at least 20 μg of antibody should be attached to the vesicles per micromole of lipid material. For vesicles having a mean number average diameter of about 1000 A°, at least 40 μg of antibody should be attached per micromole of lipid material in the vesicles. The minimum weight of antibody attachment for larger or smaller vesicles can be calculated by extrapolation or interpolation of the requirements given above for 1000 A° and 2000 A° vesicles.

The antibody employed in preparing the reagents of the invention is advantageously provided in a high titer solution or in a purified form such as is obtainable by monoclonal production techniques. Such techniques are well-known; see for example U.S. Pat. No. 4,196,265. Monoclonal antibodies are highly specific in their binding characteristics, affinity and uniformity.

The sensitized reagents of the invention, prepared as described above may be lyophilized employing conventional freeze-drying techniques and apparatus. The lyophilized reagent may be stored for extended periods of time, reconstituted with water and used with only minimal loss of sensitivity.

The method of the invention may be carried out employing the reagents of the invention.

Immunoassay for a given organic compound may be carried out in at least three different procedures, using the reagents of the invention. In the first procedure, lysis of the vesicles is carried out with the use of complement or lytic components of complement. The assay is carried out by mixing the reagent lipid vesicles with the ligand containing solution (analyte), in an aqueous buffered medium. The buffered medium may be a buffer of trihydroxymethyl aminomethane, phosphate, carbonate, borate and the like, advantageously having a pH within the range of from 6 to 9 and an osmolarity near that of the encapsulated reporter composition. Advantageously the buffer medium will also contain inorganic salts such as sodium, magnesium and calcium chlorides. The presence of calcium ion is particularly advantageous. The mixture of analyte and lipid vesicle reagent may then be incubated for a time sufficient to bind the analyte to the reagent's antibody component. Incubations will generally be at a temperature of from about 4° to 40° C., more usually from about 20° to 37° C. The time for incubation will generally vary from about 5 minutes to 1 hour, more usually from about 10 minutes to about 45 minutes, depending in part on the temperature of incubation.

The concentration of analyte which may be assayed will generally vary from about $10^{-4}$ to $10^{-15}$M, more usually from about $10^{-6}$ to $10^{-13}$M. Considerations such as whether the assay is qualitative, semi-quantitative or quantitative, the particular detection technique and the concentration of the analyte of interest will normally determine the concentrations of the lipid vesicle reagent added to the analyte.

While the concentrations of the reagent will generally be determined by the concentration range of interest of the analyte, the final concentration of the reagent will normally be determined empirically to optimize the sensitivity of the assay over the range of interest.

Following incubation, or even during incubation, the lysing agent (complement) may be added. The complement presence will make those sensitized lipid vesicles that have an antibody-antigen complex on the vesicle surface more permeable than those to which no antigen has bound. The rate and extent in the increase in permeability is a function of the amount or number of the complexes formed per vesicle. This can be adjusted by altering the amount of antibody attached to the lipid vesicle surface, the amount of complement added, the temperature of the reaction, the affinity of the antibody for the ligand, the size of the lipid vesicle and the lipid composition of the vesicle. Each of these factors may be adjustedd for, as desired, for optional results. The degree of lysis may be detected by visual observation of the released reporter composition, etc., advantageously using an appropriate instrument for detecting the reporter composition release, i.e.; spectrophotometer, fluormeter, etc. In this way, the assay is done without requiring separation of reagents that have bound the substance to be assayed (the analyte) from those that have not. Standard assay media can be prepared which have known amounts of analyte. The observed signals with the standard assay media may then be graphed, so as to relate concentration to signal. Once a standard curve has been established, a signal may be directly related to the concentration of the analyte.

The second procedure involves allowing antibody e.g. mouse anti-analyte to partition between the analyte in an unknown sample and analyte immobilized on the surface of a solid support, then allowing the lipid vesicle reagents with the encapsulated reporter and containing an anti-idiotype antibody (e.g. rabbit anti-mouse IgG) on its surface to partition between the first partitioned antibody which remains in solution and that which has bound to the solid support. Sensitized lipid vesicles that have remained in solution are then separated from those which have bound to the solid support and are then lysed with a detergent or other lytic agent. In this way a signal is obtained from vesicle that have combined with antibody that has previously combined with its homologue antigen. This second procedure requires that lipid vesicle-antibody-analyte complex formed be separated from complex on the solid support.

Antigens may be immobilized by the physical binding or chemical bonding to a solid, water-insoluble surface. Antigens, as proteins, are readily immobilized on insoluble supports and the techniques are well-known; see for example Wide, Radioimmunoassay Methods, edited by Kirkham and Hunter, (1970). Advantageously, the immobilized antigens employed in the method of the invention are immobilized by covalent bonding to a water-insoluble polysaccharide such as agarose.

The third procedure is particularly useful to employ the reagents of the invention to assay for a polyvalent immunoreactant (analyte) such as a virus, bacteria, or molecule having more than one epitopic site. The procedure is reminiscent of the well-known "sandwich technique" of immunoassay. In the method of the present invention, antibody identical to that attached to the sensitized lipid vesicle reagent is immobilized by attachment to a solid (insoluble) support such as, for example, agarose beads using the known techniques for doing so. The beads with attached antibody are dispersed in the analyte to be assayed, and the resulting dispersion may be allowed to incubate for a sufficient period to bind the analyte to the immobilized antibody. At the end of the incubation period, the solids (bound analyte) are separated and washed. The bound analyte is then mixed, in buffer, with the sensitized lipid vesicle reagents of the invention (having the same antibody component of the immobilized antibody). The sensitized lipid vesicles will "sandwich" the analyte, previously bound to the immobilized antibody, thereby associating with the insoluble material. The insoluble "sandwich" may then be separated, washed and dispersed in an appropriate fluid medium wherein lysis of the lipid vesicle component may be effected by addition of a lytic agent. Lysis occurs with release of the reporter composition as described above. Observation of the signal generated will indicate the analytical result.

The lytic agents that may be used in the assay of the invention include the complement proteins or components thereof.

Alternative to the use of complement to initiate lysis of the lipid vesicle membrane, one may carry out the method of the invention using other lytic agents. Representative of such lytic agents are surfactants.

The term "surfactant" as used herein is a contraction of "surface-active agent" and is a broadly descriptive term used to describe a chemical compound which is (1) soluble in at least one phase of a system, (2) has an amphipathic structure, (3) the molecules of which form oriented monolayers at phase interfaces, (4) exhibits an equilibrium concentration as a solute at a phase interface, greater than its concentration in the bulk of the solution, (5) forms micelles which the concentration as a solute in solution, exceeds a characteristic limiting value and (6) exhibits some combination of the functional properties of detergency, foaming, wetting, emulsifying, solubilizing and dispersing.

Representative of useful surfactants which may be used as a lytic agent in the method of the invention are anionic surfactants of the formula:

$RSO_3Na$ wherein R represents alkyl or alkylarylene such as sodium dodecylbenzenesulfonate and the like.

Preferred as the surfactant type of lytic agent are the non-ionic types. The non-ionic types of surfactant are generally well-known compounds and include, for example, the alkylphenoxypoly(ethyleneoxy)ethanols such as the octylphenoxypoly(ethyleneoxy)ethanols and nonylphenoxypoly(ethyleneoxy)ethanols having polyoxyethylene moieties of from 9 to 10 units in length. Other non-ionic surfactants which may be employed are represented by polyethylene oxides, polypropylene oxides, long chain alkyl phosphine oxides, amine oxides and the like. Preferred is the commerically available surfactant Triton X-100 (Rhom and Haas Co., Philadelphia, Pa.; an octylphenoxypoly(ethyleneoxy)ethanol wherein the polyoxyethylene chain is an average of 9-10 units in length).

Without being bound by any theory of operation, it is believed that the method of the invention utilizing complement as the lysing agent proceeds when the antibody, attached to the lipid vesicle surface, reacts with and binds the corresponding immunoreactant. When this occurs, the antibody moiety undergoes a conformational change which makes the antibody segment or portion receptive to interaction with complement. The complement presence initiates a change in the conformation of the vesicle attached antibody and lysis of the lipid vesicle membrane occurs. Lysis either allows the vesicle contents to leak out, or compounds outside of the vesicle (such as an enzyme substrate) to leak in. The extent of the complement mediated lysis is directly proportional to the quantity of ligand present in the analyte. Moreover, when lysis occurs, the signal from the released preferred encapsulated reporter composition increases.

The following examples and preparations describe the manner and process of making and using the invention and set forth the best mode contemplated by the inventor for carrying out the invention but are not to be construed as limiting. All parts are by weight unless otherwise specified.

PREPARATION 1

(A) LIPID VESICLE PREPARATION

Following the reverse phase evaporation method described in U.S. Pat. No. 4,235,871, lipid vesicles were prepared encapsulating an aqueous solution of 100 mM carboxyfluorescein. At this concentration carboxyfluorescein is self-quenched upon release from the lipid vesicle. The fluorescence intensity increases up to 20 fold. The vesicles are composed of lactosyl cerebroside, phosphatidylglycerol, phosphatidylcholine and cholesterol in molar ratios of 1:1:4:5. The vesicles so prepared are passed through a 0.4 polycarbonate membrane and suspended in saline. The lipid vesicles were separated from non-encapsulated material by column chromatography in 135 mM sodium chloride, 10 mM sodium phosphate pH 7.4.

(B) MODIFICATION OF VESICLE SURFACE

A quantity of the lipid vesicles prepared in accordance with the above procedure of Part (A) were charged to an appropriate reaction vessel. To the charge there was added with stirring a solution of 20 mM sodium metaperiodate, 135 mM sodium chloride and 10 mM sodium phosphate (pH 7.4). The resulting mixture was allowed to stand in darkness for 90 minutes at a temperature of circa 20° C. Excess periodate was removed by dialysis of the reaction mixture against 250 ml of buffered saline (135 mM sodium chloride, 10 mM sodiumphosphate) having a pH of 7.4, for 2 hours. The product was a lipid vesicle, having a surface modified by oxidation of carbohydrate hydroxyl groups to aldehyde groups.

PREPARATION 2

The procedure of Preparation 1, supra., was repeated, except that in place of the carboxyfluorescein, there was encapsulated an aqueous mixture of 10 mM terbium chloride, 100 mM sodium citrate, 2 mM 1-histidine and 2 mM of N-tris (hydroxymethyl)methyl-2-aminosulfonic acid (TES) having a pH of 7.4.

PREPARATION 3

The procedure of Preparation 1, supra., was repeated, except that in place of the carboxyfluorescein, there was encapsulated an aqueous mixture of 100 mM sodium chloride, 2 mM of tris (hydroxymethyl)aminomethane (TRIS) and 2 mM TES (pH 8.0) containing 20 mg/ml of E.coli derived alkaline phosphatase as a reporter molecule.

PREPARATION 4

Dimyristoylphosphatidylethanolamine (DMPE) (100 μmoles) was dissolved in 5 ml of anhydrous methanol containing 2 equivalents of triethylamine and 50 mg of m-maleimidobenzoyl N-hydroxysuccinimide ester (Kitagawa and Aikawa, J. Biochem. 79,233–236, 1976). The resulting reaction was allowed to proceed under a nitrogen gas atmosphere, at room temperature, overnight. The resulting reaction mixture was subjected to thin layer chromatography on Silica gel H in chloroform/methanol/water (65/25/4), which revealed quantitative conversion of the DMPE to a faster migrating product. Methanol was removed under reduced pressure and the products redissolved in chloroform. The chloroform phase was extracted twice with 1% sodium chloride and the maleimidobenzoyl-phosphatidylethanolamine (MBPE) purified by silicic acid chromatography with chloroform/methanol (4/1) as the solvent. Following purification, thin-layer chromatography indicated a single phosphate containing spot, that was ninhydrin negative. The MBPE is an activated phospholipid for coupling sulfhydryl containing compounds, including proteins, to lipid vesicles.

PREPARATION 5
LIPID VESICLE PREPARATION

The procedure of Preparation 1, Part (A) supra., was repeated, except that the vesicles prepared in Part (A) were composed of MBPE from Preparation 4, supra., phosphatidylcholine and cholesterol in molar ratios of 1:9:8 and encapsulate an aqueous solution (pH 6.0) of 100 mM calcein (fluorescein complexon).

The vesicles were separated from the unencapsulated calcein by column chromatography in 100 mM sodium chloride-2 mM sodium phosphate (pH 6.0).

EXAMPLE 1
ANTIPHTHALATE REAGENT

An appropriate vessel was charged with 1.1 ml of the Preparation 1, Part (B), supra., containing 10 μmoles of lipid vesicles. To the charge there was added with stirring 1.0 ml of monoclonal antiphthalate (antibody; 3.0 mg protein) and 0.2 ml of a 200 mM sodium cyanoborohydride solution. The resulting reaction mixture was allowed to stand overnight while maintained at a temperature of 4° C. At the end of this period of time, the reaction mixture was separated on a Biogel A5M agarose column (Biorad, Richmond, Ca.; 1.5×37 cm). Assay of the lipid vesicle fraction (standard protein assay) shows 0.74 mg. of antibody attached to 10 μmoles of lipid (74 μg/μmole of lipid).

EXAMPLE 2
IMMUNOASSAY

To 0.06 μmoles of the antiphthalate lipid vesicles from Example 1, supra., there was added 2.5 ml of buffered saline containing 1 mM of calcium chloride to obtain a vesicle dispersion. To each of a series of six vessels containing various concentrations of sodium phthalate (pH 7.4) solution, there was added 0.025 ml of antiphthalate vesicle dispersion. The resulting mixture was incubated at a temperature of 37° C. for 5 minutes. At the end of this period, 0.025 ml. of freshly prepared guinea pig complement was added and the resulting lysis allowed to proceed while the vessels were placed in a spectrofluorimeter and maintained at a temperature of 37° C. The spectrofluorimeter was adjusted for an excitation wavelength at 490 nm and an emission wavelength at 520 nm. The difference between the fluorescent signal at the end of 15 minutes of incubation in the presence of complement and the signal immediately after complement addition is a measure of the extent of lysis. The relative fluorescence observed is reported in the following Table 1. For control purposes, the procedure was repeated using vessels containing no sodium phthalate; to which the lipid vesicles are not added; to which heat-inactivated complement was added; and to which no complement was added.

TABLE 1

| Concentration Phthalate | (n moles/ml) relative fluorescence |
|---|---|
| 0 | 0.1 |
| 4 | 0.3 |
| 8 | 0.8 |
| 40 | 1.9 |
| 80 | 6.1 |
| 400 | 9.0 |
| 2000 | 13.0 |
| no antibody | 0.3 |
| inactivated complement | 0.5 |
| no complement | 0.0 |

The results shown in Table 1 above indicated a phthalate dependent increase in carboxyfluorecein release that occurs in the presence of complement and lipid vesicles containing the antiphthalate antibody chemically bonded on the vesicle surface.

EXAMPLE 3
REAGENT PREPARATION

The procedure of Example 1, supra., was repeated, except that the surface-modified lipid vesicles of Preparation 1, supra., as used therein is replaced with the surface-modified lipid vesicles of Preparation 2, supra. The resulting lipid vesicle bearing the antiphthalate antibody were suspended in a buffer solution of 100 mM sodium dipicolinate (DPA), 2 mM histidine, 2 mM TES and 1 mM calcium chloride (pH 7.4).

EXAMPLE 4
IMMUNOASSAY

Equal proportions of the product of Example 3, supra., were charged to two vessels. To one vessel there was added 1 nmole of sodium phthalate and both vessels with contents were incubated at a temperature of 37° C. for 5 minutes. At the end of this period, freshly prepared guinea pig complement was added and the fluorescence signal measured as described in Example 2, supra., employing an excitation wavelength of 276 nm and an emission wavelength of 491 nm. The incubation was continued for 15 minutes and the fluorescence measured again. Control runs showed that in the absence of phthalate or complement the fluorescence increased 1.6 units. In the presence of phthalate and complement the relative fluorescence increased 97 units.

EXAMPLE 5
ASSAY OF ANALYTE BY ENZYME AMPLIFICATION

The procedure of Example 1, supra., is repeated, except that the surface-modified lipid vesicles of Preparation 1, supra., are replaced with the surface-modified vesicles of Preparation 3, supra. The resulting lipid vesicles bearing antiphthalate antibody are suspended in an aqueous buffer solution of 1 mM p-nitrophenol phosphate, 1 mM calcium chloride, 2.5 mM magnesium chloride, 100 mM sodium chloride, 2 mM TRIS and 2 mM TES (pH 8.0).

EXAMPLE 6
ASSAY OF ANALYTE BY COMPLEXATION AMPLIFICATION SYSTEM

Equal proportions of the product of Example 5, supra., are charged to each of two vessels. To one vessel there is added with stirring 1 n mole of sodium phthalate. After a 5 minute incubation at a temperature of 37° C. freshly prepared guinea pig complement is added and the reaction is allowed to proceed for 30 minutes at a temperature of 37° C. At the end of this period an equal volume of 100 mM tris/HCL buffer (pH 8.0) containing 1% Triton X-100, supra., is added and the absorbance is immediately read at 405 nm in a spectrophotometer against a blank treated in the same way as the test and consisting of all the reagents except the sodium phthalate. The difference between the blank and the test is a measure of the amount of analyte present in the unknown and can be quantitated by reference to a standard curve. The absorbance increases in a dose dependent fashion with increasing amounts of phthalate. A wide variety of enzymes can be encapsulated in the liposome to serve as the amplification system. The enzymes are used with the appropriate substrates as is readily apparent to those skilled in the art (see for example U.S. Pat. No. 4,193,983).

EXAMPLE 7

Freshly separated lipid vesicles from Preparation 5, supra., was incubated with antiphthalate monoclonal antibody (1 mg/ml) that previously had between 2-4 reactive sulfhydryl groups placed on them by the method of Carlsson et al, Biochem. J., 173, 723–737 (1978). The incubation was done in a total volume of 21 ml in the phosphate buffer pH 6.0 for 12 hours at room temperature under a blanket of nitrogen gas. Lipid vesicles containing the antiphthalate antibody were separated from the unattached antibody by column chromatography on agarose gels in 100 mM sodium chloride—10 mM sodium phosphate (pH 7.4). Under these conditions approximately 175 $\mu$g protein are coupled to a 1 $\mu$mole of lipid.

Incubation of 5 nmoles of lipid vesicles containing the antibody in 0.2 ml of 100 mM sodium chloride-2 mM histidine-1,5 mM calcium chloride at 37° C. in the presence of phthalate and fresh complement for 15 minutes results in the lysis of the vesicle and the release of calcein. The extent of lysis increases with increasing concentrations of phthalate. Incubation of the vesicles in the absence of either phthalate or complement results in no lysis of the vesicles and no increase of the signal from calcein.

EXAMPLE 8

ATTACHMENT OF ANTIBODY FOLLOWING GENERATION OF ALDEHYDE ON THE VESICLE BY TREATMENT WITH GALACTOSE OXIDASE

A portion of the lipid vesicles prepared according to the procedure of Preparation 1, supra., encapsulating carboxyfluorescein was provided.

To attach the antibody to the vesicle surface the C-6 hydroxyl group on the galactose residue of the lactosylcerebroside was oxidized to an aldehyde by the enzyme galactose oxidase as detailed by Zile et al, J. Biochem., 254,3 547-3553 (1979). 5 $\mu$moles of the vesicle lipid was incubated with 25 units of galactose oxidase (Sigma Corp.) in saline for 4 hours at a temperature of 37° C. Lipid vesicles containing an aldehyde group on their surface are separated from the enzyme by column chromatography. The fraction containing the vesicles was mixed with 2 mg of antiphthalate antibody and 0.2 ml of a freshly prepared solution of sodium cyanoborohydride and allowed to react at room temperature overnight. The vesicles containing the antibody on their surface are separated from non-attached antibody. The resulting vesicles are suitable for use in the immunoassay described in Example 2.

EXAMPLE 9

PREPARATION OF A UNIVERSAL IMMUNOASSAY REAGENT

A rabbit antimouse antibody was treated with pepsin to form an F(ab')$_2$ fragment. This fragment retains the two antimouse antibody binding sites but does not have the region that is recognized by complement. The fragment was incubated for 90 min. with 20 mM dithiothreotol in 50 mM sodium acetate pH 5.5 under nitrogen gas at room temperature. The resulting Fab' fragments were separated from the dithiothreitol on a Sephadex G-25 column and immediately mixed with lipid vesicles composed of MBPE/phosphatidylcholine/cholesterol: 1/9/8 as described in Preparation 5, supra., and incubated for 12 hours at room temperature and under a blanket of nitrogen gas. The vesicles with rabbit antimouse Fab' fragments attached can now be mixed with any mouse antibody to form an immunoassay reagent. 50 nmoles of lipid vesicle containing 4 $\mu$g of rabbit antimouse Fab' fragments were incubated for 30 minutes with 50 $\mu$g of mouse antiphthalate monoclonal antibody in 1 ml of saline. Mouse antibody that did not become attached to the vesicle was separated from the vesicle antibody complex by centrifugation at 12,000×G for 15 minutes. The vesicle antibody complex is resuspended in 1 ml of 0.1 M sodium chloride, 2 mM histidine 1 mM calcium chloride and 100 $\mu$l of the vesicles is mixed with 10 $\mu$l of the phthalate solution and 15 $\mu$l of complement for 15 minutes. At the end of this period lysis is quantitated by the release of the calcein and is proportional to the amount of phthalate added (from 0.1 to 2 nmoles). In the absence of complement no increase in lysis will be observed.

In a similar fashion assays for other organic ligand substances can be prepared by adding mouse antibodies with binding sites for other antigens. A wide range of anti-immunoglobulin Fab' fragments such as the F(ab') and F(ab')$_2$ fragments can be prepared and used to form a flexible immunoassay procedure.

EXAMPLE 10

ATTACHMENT OF ANTIBODY TO THE LIPID VESICLES THROUGH A TETRADECYLMELIBIONAMIDE ACTIVATED BY 1,1'-CARBONYDIIMIDAZOLE TO FORM AN IMMUNOASSAY REAGENT

Tetradecylmelibionamide (1 mmole) synthesized as described by Williams et al., Arch. Biochem. Biophys., 195, 145–151 (1979) was placed in acetone and activated by adding 1 m mole of 1,1-carbonyldiimidazole as described in Bethell et al., J. Biol. Chem., 254, 2572-2574 (1979). Then 10 nmoles of the activated reagent was mixed with 1 mg of mouse antiphthalate antibody in 1 ml of 50 mM sodium phosphate-50 mM sodium chloride and allowed to incubate overnight at room temperature. The reaction mixture was then incubated with 5 $\mu$moles of lipid vesicles composed of phosphatidylcholine/phosphatidylethanolamine/cholesterol (9/1/5) containing 100 mM of calcein prepared as described in U.S. Pat. No. 4,235,871.

The mouse antiphthalate immunoglobulin which now has a hydrophobic alkyl chain attached to it, tightly associates with the lipid vesicle membrane due to hydrophobic forces. Antibody that does not become associated is separated by gel filtration. The antibody-vesicle reagent can be used in an immunoassay as described in Example 2, supra.

EXAMPLE 11

THE USE OF SURFACTANTS AS LYTIC AGENTS IN THE IMMUNOASSAY

Lipid vesicles entrapping calcein and having mouse antiphthalate on their surface were prepared as described in Example 6, supra. The vesicles (19 nmoles of lipid in 1 ml) were incubated with 100 picomoles of phthalate for 30 minutes at a temperature of 37° C. At the end of this incubation, agarose beads containing aminophthalate attached to the bead surface by the method of Cuatrecasas and Parikh, Biochemistry, 11,2291–2299 (1972) were added to the assay mixture and the mixture allowed to incubate while being gently mixed for 30 minutes. The resulting mixture was allowed to stand for 30 minutes and the beads then separated from the solution by decantation. Vesicles which have reacted with phthalate in the first step do not bind to the beads and remain in solution while those that did not bind to phthalate in the first step bind to the phthalate exposed on the beads. A surfactant (Triton X-100, supra.; 0.05 ml) was added to the solution which contains the vesicles not attached to the beads, to lyse the vesicles, releasing entrapped calcein. The increase in fluorescence signal from the released calcein was proportional to the amount of phthalate in the original suspension. This forms the basis for an immunoassay for any substance to which an antibody can be made and does not require the use of complement to lyse the lipid vesicles.

EXAMPLE 12

A UNIVERSAL REAGENT FOR USE IN THE IMMUNOASSAY WHICH USES SURFACTANT TO LYSE THE LIPID VESICLE

Lipid vesicles entrapping calcein and having a rabbit antimouse antibody on their surface are prepared as described in Example 10, supra. These are a universal reagent which can be used with any mouse antibody to prepare an immunoassay kit for the antigen recognized by the particcular antibody used. To assay for the levels of a particcular antigen, in this case phthalate, mouse antiphthalate antibody is first incubated for 30 minutes with 1 nmole of phthalate in 1 ml of saline. The mixture is then added to a test tube containing 10 mg of agarose beads containing aminophthalate attached to the bead surface as described in Example 11, supra., and incubated for an additional 30 minutes with gentle shaking. A defined amount (50 nmoles) of vesicles having the rabbit antimouse antibody on their surface are added to the mixture and the incubation is continued for 30 minutes more. The beads are then allowed to settle for 10 minutes. The supernatent solution is decanted off of the beads and poured into a tube containing a detergent solution 0.5% Triton X-100 which lysis the vesicles that remain in the solution. The signal from the released calcein is directly related to the amount of phthalate in the original solution. In a similar fashion a wide variety of other analytes can be assayed for, limited only by one's ability to provide antibody to the analyte.

EXAMPLE 13

A UNIVERSAL REAGENT

In addition to antibodies that can recognize antibodies, e.g.; rabbit antimouse immunoglobins, certain proteins bind to the constant region of antibody molecules. One such protein is produced by the bacterial *Staphylococcus aureus* called protein A. This protein can be attached to the lipid vesicle surface by the procedure given in Example 6, supra., and when used in the assay procedure described in Example 12 can be used in the immunoassay of the invention.

EXAMPLE 14

LYOPHILIZATION OF IMMUNOASSAY REAGENT

Lipid vesicles encapsulating alkaline phosphatase and with rabbit antimouse Fab' fragments on their surface are prepared as described in Example 7, supra., and are then freeze dried. After rehydration with distilled water and incubation for 30 minutes at a temperature of 37° C. the vesicles are mixed with mouse antiphthalate antibody to obtain a reagent of the invention which may be used in an immunoassay, carried out as described in Example 7, supra.

The invention also comprises diagnostic kits, containing reagents of the invention and which are useful for the determination of the presence or absence of ligands in biological fluids such as blood, blood serum, saliva, urine and the like. The kits are particularly useful for the detection and immunoassay of reagins, immunoglobulins and the like. The diagnostic kits of the invention comprise a container, housing in appropriate vessels (1) a reagent of the invention as described above, (2) a lytic agent and optionally (3) buffer solutions, (4) positive control solutions of known ligands in known concentrations and (5) amplification system components as desired to suspend the reagents of the invention in.

What is claimed:

1. An immunoreactive liposome reagent for use in the determination of a chemical compound capable of entering into an immunospecific reaction with a known antibody, said reagent comprising
    a suspension of liposomes containing reporter molecules, and
    a surface array of molecules of such antibody attached to the liposomes through glycolipid molecules anchored in the liposomes and linked to the antibody molecules by a diimidazole coupling agent.

2. The reagent of claim 1, wherein the glycolipid is a melibionamide and the diimidazole coupling agent is 1,1-carbonyldiimidazole.

3. The reagent of claim 2, wherein the melibionamide is tetradecylmelibionamide.

4. A method of producing an immunoreactive liposome reagent having an array of surface-bound antibody molecules, said method comprising
    providing a glycolipid,
    linking such antibody molecules covalently to molecules of the glycolipid, in an aqueous medium, with a diimidazole coupling agent, and
    mixing the resultant antibody-glycolipid couple with liposomes in an aqueous medium to produce binding of the antibody to the liposome surface through the linked glycolipid.

5. The method of claim 4, wherein the glycolipid provided is a melibionamide.

6. The method of claim 5, wherein the melibionamide provided is tetradecylmelibionamide.

7. The method of claim 5, wherein the diimidazole is 1,1-carbonyldiimidazole.

8. The method of claim 5, wherein said linking is performed in the absence of a detergent.

9. The method of claim 8, wherein said mixing is also performed in the absence of a detergent to produce a liposome reagent free of contaminating detergent.

* * * * *